United States Patent
Tse et al.

(10) Patent No.: US 9,890,302 B2
(45) Date of Patent: Feb. 13, 2018

(54) ADHESIVE ARTICLE INCLUDING PRIMER LAYER AND METHOD OF MAKING THE SAME

(71) Applicant: 3M INNOVATIVE PROPERTIES COMPANY, St. Paul, MN (US)

(72) Inventors: Kiu-Yuen Tse, Woodbury, MN (US); Michael D. Determan, Mahtomedi, MN (US); David T. Amos, St. Paul, MN (US); Daniel C. Munson, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 709 days.

(21) Appl. No.: 14/367,497

(22) PCT Filed: Dec. 20, 2012

(86) PCT No.: PCT/US2012/070765
§ 371 (c)(1),
(2) Date: Jun. 20, 2014

(87) PCT Pub. No.: WO2013/096530
PCT Pub. Date: Jun. 27, 2013

(65) Prior Publication Data
US 2014/0358104 A1    Dec. 4, 2014

Related U.S. Application Data

(60) Provisional application No. 61/579,115, filed on Dec. 22, 2011.

(51) Int. Cl.
*B32B 7/12* (2006.01)
*C09J 7/02* (2006.01)
(Continued)

(52) U.S. Cl.
CPC ......... *C09J 7/0207* (2013.01); *A61F 13/0253* (2013.01); *A61L 15/225* (2013.01);
(Continued)

(58) Field of Classification Search
CPC ..... C09J 7/0207; A61F 13/0253; B05D 3/068
See application file for complete search history.

(56) References Cited

U.S. PATENT DOCUMENTS

| 2,676,182 A | 4/1954 | Daudt |
| 2,736,721 A | 2/1956 | Dexter |

(Continued)

FOREIGN PATENT DOCUMENTS

| JP | H02-36234 | 2/1990 |
| JP | 2008-143923 | 6/2008 |

(Continued)

OTHER PUBLICATIONS

Mark, "Encyclopedia of Polymer Science and Engineering", vol. 15, 1989, pp. 265-270.

(Continued)

*Primary Examiner* — Victor S Chang

(57) ABSTRACT

Adhesive articles that include a substrate, a silicone polyoxamide-containing primer layer, and a silicone adhesive are disclosed. Methods of making the adhesive articles and the use of a silicone polyoxamide as a primer for improving adhesion between a substrate and a silicone adhesive are also disclosed.

20 Claims, 1 Drawing Sheet

(51) Int. Cl.
*C09J 183/04* (2006.01)
*A61F 13/02* (2006.01)
*A61L 15/22* (2006.01)
*A61L 15/58* (2006.01)
*B05D 3/06* (2006.01)
*C09J 183/10* (2006.01)
*C08G 77/455* (2006.01)

(52) U.S. Cl.
CPC ............ *A61L 15/585* (2013.01); *B05D 3/068* (2013.01); *C09J 183/04* (2013.01); *C09J 183/10* (2013.01); *B32B 2405/00* (2013.01); *C08G 77/455* (2013.01); *C09J 2483/00* (2013.01); *C09J 2483/003* (2013.01); *Y10T 428/2809* (2015.01); *Y10T 428/2843* (2015.01); *Y10T 442/2098* (2015.04)

(56) References Cited

U.S. PATENT DOCUMENTS

| | | |
|---|---|---|
| 3,627,851 A | 12/1971 | Brady |
| 3,772,247 A | 11/1973 | Flannigan |
| 4,935,484 A | 6/1990 | Wolfgruber |
| 5,082,706 A | 1/1992 | Tangney |
| 5,110,890 A | 5/1992 | Butler |
| 5,248,739 A | 9/1993 | Schmidt |
| 5,302,685 A | 4/1994 | Tsumura |
| 5,319,040 A | 6/1994 | Wengrovius |
| 5,891,530 A | 4/1999 | Wright |
| 6,129,971 A | 10/2000 | Brandt |
| 6,500,526 B1 | 12/2002 | Hannington |
| 7,371,464 B2 | 5/2008 | Sherman |
| 7,915,370 B2 | 3/2011 | Sherman |
| 8,557,378 B2 | 10/2013 | Yamanaka |
| 2003/0104224 A1 | 6/2003 | Kuroda |
| 2003/0165676 A1 | 9/2003 | Zhou |
| 2004/0185258 A1 | 9/2004 | Fukushi |
| 2005/0136266 A1* | 6/2005 | Zhou ................. A61L 15/58 428/447 |
| 2007/0100306 A1 | 5/2007 | DiZio et al. |
| 2007/0177272 A1* | 8/2007 | Benson ................. B32B 27/28 359/584 |
| 2008/0187750 A1 | 8/2008 | Sherman |
| 2009/0229732 A1 | 9/2009 | Determan |
| 2011/0071268 A1* | 3/2011 | Hays ................. C08G 77/455 528/26 |
| 2011/0212325 A1 | 9/2011 | Determan |

FOREIGN PATENT DOCUMENTS

| | | |
|---|---|---|
| JP | 2010-184953 | 8/2010 |
| WO | WO 2005-102403 | 11/2005 |
| WO | WO 2009-114683 | 9/2009 |
| WO | WO 2010-056543 | 5/2010 |
| WO | WO 2010-056544 | 5/2010 |
| WO | WO 2010-080567 | 7/2010 |
| WO | WO 2011-068754 | 6/2011 |
| WO | WO 2013-025955 | 2/2013 |
| WO | WO 2013-096535 | 6/2013 |

OTHER PUBLICATIONS

International Search Report for PCT International Application No. PCT/US2012/070765, dated Feb. 25, 2013, 5pgs.

* cited by examiner

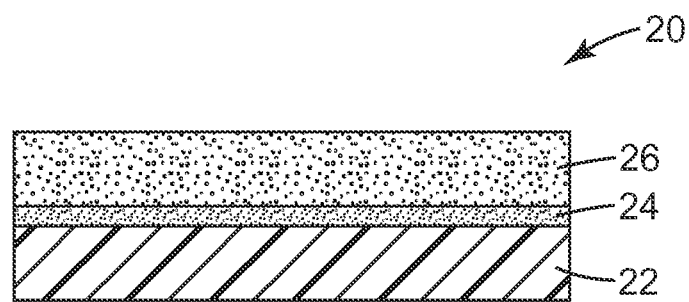

US 9,890,302 B2

ADHESIVE ARTICLE INCLUDING PRIMER LAYER AND METHOD OF MAKING THE SAME

CROSS REFERENCE TO RELATED APPLICATIONS

This application is a national stage filing under 35 U.S.C. 371 of PCT/US2012/070765, filed Dec. 20, 2012, which claims priority to U.S. Application No. 61/579,115, filed Dec. 22, 2011, the disclosure of which is incorporated by reference in its entirety herein.

BACKGROUND

Silicone adhesives, including silicone pressure sensitive adhesives, may have a variety of desirable properties. In a variety of applications, silicone adhesives may exhibit, for example, good adhesion over a wide temperature range, resistance to environmental factors such as oxidation and ultraviolet light, high moisture vapor transmission rates, and good electrical properties. Certain silicone adhesives are useful for medical tapes and dressings because the silicone adhesive can provide adhesion while gently removing from the skin without causing trauma or stripping skin cells or hair. Some of these silicone adhesives are described in U.S. Pat. App. Pub. No. 2011/0212325 (Determan et al.) and Int. Pat. App. Pub. No. WO 2005/102403 (Gantner et al.).

In certain silicone adhesive tapes, delamination of the silicone adhesive from the tape backing can be a problem. Such delamination can make it difficult to remove the adhesive from skin, for example, and limits the ability to reuse the tape.

SUMMARY

The present disclosure provides adhesive articles that include a silicone adhesive and a substrate, with a primer layer interposed between the silicone adhesive and the substrate. The primer layer includes a silicone polyoxamide. The primer layer typically improves the adhesion between the silicone adhesive and a wide variety of substrates. The adhesion is improved even though the silicone polyoxamide does not contain reactive functional groups that can bond with the substrate and/or the silicone adhesive. The primer layer in the articles disclosed herein is typically more effective than other primers for improving the adhesion between the substrate and the silicone adhesive.

In one aspect, the present disclosure provides an adhesive article that includes a substrate, a primer layer disposed on the substrate, wherein the primer layer includes a silicone polyoxamide, and a silicone adhesive disposed on the primer layer.

In another aspect, the present disclosure provides a method of making such an adhesive article. The method includes coating the primer layer onto the substrate, coating a silicone adhesive composition onto the primer layer, and crosslinking the silicone adhesive composition to form the silicone adhesive. In some embodiments, crosslinking comprises exposing the silicon adhesive composition to radiation to form a radiation crosslinked silicone adhesive. In some of these embodiments, radiation includes at least one of electron-beam or gamma radiation.

In another aspect, the present disclosure provides the use of a silicone polyoxamide as a primer for improving adhesion between a substrate and a silicone adhesive.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

"Alkyl", "alkyenyl", and the prefix "alk-" are inclusive of both straight chain and branched chain alkyl groups. Alkyl and alkenyl groups can have up to 30 carbons (in some embodiments, up to 20, 15, 12, 10, 8, 7, 6, or 5 carbons) unless otherwise specified.

"Cycloalkyl" includes monocyclic or polycyclic groups having from 3 to 10 (in some embodiments, 3 to 6 or 5 to 6) ring carbon atoms.

"Alkylene" refers to a multivalent (e.g., divalent) form of the "alkyl" groups defined above.

"Arylalkylene" refers to an "alkylene" moiety to which an aryl group is attached.

The term "aryl" as used herein includes carbocyclic aromatic rings or ring systems, for example, having 1, 2, or 3 rings and optionally containing at least one heteroatom (e.g., O, S, or N) in the ring. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

The term "polyurethane" as used herein includes compounds having more than one carbamate and/or urea group and can also contain biuret, allophanate, uretdione, or isocyanurate linkages in any combination.

Number average molecular weights can be measured, for example, by gel permeation chromatography (i.e., size exclusion chromatography) or by nuclear magnetic resonance spectroscopy using techniques known in the art.

The term "pressure sensitive adhesive" as used herein refer to adhesives that possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as PSAs are polymers designed and formulated to exhibit the requisite viscoelastic properties resulting in a desired balance of tack, peel adhesion, and shear holding power.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which:

FIG. 1 is a schematic side view of an embodiment of an adhesive article according to the present disclosure.

While the above-identified drawings and figures set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of this invention. The figures may not be drawn to scale.

DETAILED DESCRIPTION

FIG. 1 is a schematic side view of an embodiment of an adhesive article 20. In adhesive article 20, primer layer 24 is disposed on substrate 22. Silicone adhesive 26 is disposed on the primer layer. It should be understood that each of the substrate 22, primer layer 24, and silicone adhesive 26 are distinct elements of adhesive article 20.

A variety of substrates 22 may be useful in the adhesive articles disclosed herein. Exemplary suitable substrates 22 include cloth (e.g., woven cloth), nonwovens, paper and polymer-coated paper, foam backings, metals, glass, ceramics, composites, natural macromolecular materials (e.g., collagen, wood, cork, and leather), polymeric films (e.g., thermoplastic films), and combinations thereof. In some embodiments, the substrate is a paper substrate. In some embodiments, the substrate is a polymer-coated paper. In some embodiments, the substrate is a polymer (e.g., thermoplastic) film. Suitable thermoplastic substrates include polyolefins (e.g., polypropylene, polyethylene, copolymers of polypropylene and polyethylene, low density polyethylene, high density polyethylene, and linear low density polyethylene), polyesters (e.g., polyethylene terephthalate), polycarbonates, cellulose acetates, polyurethanes, and ethylene-vinyl acetate copolymer. Thermoplastic substrates may be formed in variety of ways, for example, solution casting or melt casting the thermoplastic into a film.

In some embodiments, substrates 22 included in the adhesive articles according to and/or made according to the present disclosure include a thermoplastic polyurethane, a thermoplastic polyester, or a combination thereof. The thermoplastic polyurethane or thermoplastic polyester may be selected to have a high moisture vapor rate. Such substrates are useful, for example, in wound dressings and bandages. In some embodiments, the substrate includes a thermoplastic polyurethane. A variety of thermoplastic polyurethanes may be useful, including polyether-based polyurethanes and polyester-based polyurethanes. For example, a polyether or polyester with isocyanate-reactive terminal groups may be reacted with an aryl, alkyl, arylalkylenyl, or cycloalkyl diisocyanate to provide a useful polyurethane. Exemplary suitable polyurethanes include those commercially available, for example, from Lubrizol, Wickliffe, Ohio, under the trade designation "ESTANE" (e.g., "ESTANE 58237", "ESTANE 58309", or "ESTANE 58213") and from Huntsman, The Woodlands, Tex., under the trade designation "IROGRAN" (e.g., "IROGRAN A 60 E 4902"). A variety of thermoplastic polyesters may also be useful. Exemplary suitable polyesters include those commercially available, for example, from Mitsubishi, Greer, S.C., under the trade designation "HOSTAPHAN 3SAB" polyester film and from E.I. du Pont de Nemours and Company, Wilmington, Del., under the trade designation "HYTREL".

In some embodiments, the substrate is porous (e.g., a nonwoven or cloth substrate). In these embodiments, the primer layer provides an additional advantage to the adhesive article disclosed herein in that the primer layer prevents the adhesive from flowing through the substrate. This barrier property of the primer layer may depend, for example, on the thickness of the primer layer.

The primer layer 24 in the adhesive article according to and/or made according to the present disclosure includes a silicone polyoxamide. In some embodiments, the primer layer consists of a silicone polyoxamide or a mixture of silicone polyoxamides. In some embodiments, the silicone polyoxamide is a linear silicone polyoxamide. In some embodiments, the silicone polyoxamide has at least two repeat units represented by Formula I:

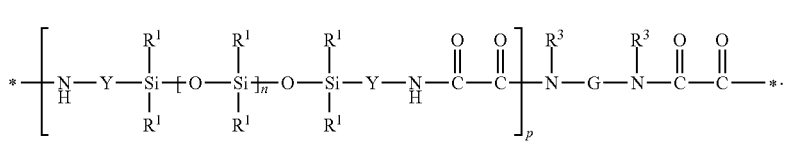

In Formula I, each $R^1$ is independently an alkyl, haloalkyl, arylalkylenyl, alkenyl, aryl, or aryl substituted with an alkyl, alkoxy, or halo, each Y is independently an alkylene, alkylarylene, or arylalkylene, and each G is independently alkylene, arylene, arylalkylene, alkylarylene, polyoxyalkylene, or polydiorganosiloxane. $R^3$ is hydrogen or alkyl or $R^3$ taken together with G and with the nitrogen to which they are both attached forms a heterocyclic group, n is independently in a range from 40 to 1500, p is in a range from 1 to 10; and the asterisk (*) indicates a site of attachment of the repeat unit to another group in the copolymer, for example, another repeat unit of Formula I.

Suitable alkyl groups for $R^1$ in Formula I have, in some embodiments, 1 to 10, 1 to 6, or 1 to 4 carbon atoms. Exemplary alkyl groups $R^1$ in Formula I include methyl, ethyl, isopropyl, n-propyl, n-butyl, and iso-butyl. Suitable haloalkyl groups for $R^1$ often have only a portion of the hydrogen atoms of the corresponding alkyl group replaced with a halogen. Exemplary haloalkyl groups include chloroalkyl and fluoroalkyl groups with 1 to 3 halogen atoms and 3 to 10 carbon atoms. Suitable alkenyl groups for $R^1$ have, in some embodiments, 2 to 10 carbon atoms. Exemplary alkenyl groups often have 2 to 8, 2 to 6, or 2 to 4 carbon atoms such as ethenyl, n-propenyl, and n-butenyl. Suitable aryl groups for $R^1$ often have 6 to 12 carbon atoms. Phenyl is an exemplary aryl group. The aryl group can be unsubstituted or substituted with an alkyl (e.g., an alkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), or halo (e.g., chloro, bromo, or fluoro). Suitable arylalkylenyl groups for $R^1$ usually have an alkylene group with 1 to 10 carbon atoms and an aryl group with 6 to 12 carbon atoms. In some exemplary arylalkylenyl groups, the aryl group is phenyl and the alkylene group has 1 to 10 carbon atoms, 1 to 6 carbon atoms, or 1 to 4 carbon atoms (i.e., the structure of the arylalkylenyl is alkylene-phenyl where an alkylene is bonded to a phenyl group).

In some embodiments, in some repeat units of Formula I, at least 40 percent, or at least 50 percent, of the $R^1$ groups are phenyl, methyl, or combinations thereof. For example, at least 60 percent, at least 70 percent, at least 80 percent, at least 90 percent, at least 95 percent, at least 98 percent, or at least 99 percent of the $R^1$ groups can be phenyl, methyl, or combinations thereof. In some embodiments, in some repeat units of Formula I, at least 40 percent, or at least 50 percent, of the $R^1$ groups are methyl. For example, at least 60 percent, at least 70 percent, at least 80 percent, at least 90 percent, at least 95 percent, at least 98 percent, or at least 99 percent of the $R^1$ groups can be methyl. The remaining $R^1$ groups can be selected from an alkyl having at least two carbon atoms, haloalkyl, arylalkylenyl, alkenyl, aryl, or aryl substituted with an alkyl, alkoxy, or halo.

Each Y in Formula I is independently an alkylene, arylalkylene, or alkylarylene. In some embodiments, suitable alkylene groups typically have up to 10 carbon atoms, up to 8 carbon atoms, up to 6 carbon atoms, or up to 4 carbon atoms. Exemplary alkylene groups include methylene, ethylene, propylene, and butylene. Suitable arylalkylene and alkylarylene groups usually have an arylene group with 6 to 12 carbon atoms bonded to an alkylene group with 1 to 10 carbon atoms. In some exemplary arylalkylene and alkylarylene groups, the arylene portion is phenylene. That is, the divalent arylalkylene or alkylarylene group is phenylene-alkylene or alkylene-phenylene where the phenylene is bonded to an alkylene having 1 to 10, 1 to 8, 1 to 6, or 1 to 4 carbon atoms.

Each subscript n in Formula I is independently in a range from 40 to 1500. For example, subscript n can be up to 1000, up to 500, up to 400, up to 300, up to 200, up to 100, up to 80, or up to 60. In some embodiments, subscript n can be in the range of 40 to 1500, 40 to 1000, 40 to 500, 50 to 1500, 50 to 1000, 50 to 500, or 100 to 1000.

The subscript p is in a range from 1 to 10. For example, the value of p can be up to 9, up to 8, up to 7, up to 6, up to 5, up to 4, up to 3, or up to 2. In some embodiments, the value of p is in the range of 1 to 8, 1 to 6, or 1 to 4.

In Formula I, each G is independently an alkylene, arylene, arylalkylene, alkylarylene, polyoxyalkyene, or polydiorganosiloxane. Suitable alkylenes often have 2 to 10, 2 to 6, or 2 to 4 carbon atoms. Exemplary alkylene groups include ethylene, propylene, and butylene. In some embodiments, G is ethylene. Suitable polyoxyalkylenes include polyoxyethylene having at least 2 ethylene units, polyoxypropylene having at least 2 propylene units, or copolymers thereof. Exemplary polydiorganosiloxanes include, but are not limited to, polydimethylsiloxanes with alkylene terminal groups. Suitable arylalkylene and alkylarylene groups usually contain an arylene group having 6 to 12 carbon atoms bonded to an alkylene group having 1 to 10 carbon atoms. Some exemplary arylalkylene and alkylarylene groups are phenylene-alkylene and alkylene-phenylene where the phenylene is bonded to an alkylene having 1 to 10 carbon atoms, 1 to 8 carbon atoms, 1 to 6 carbon atoms, or 1 to 4 carbon atoms. Group G in Formula I is typically derived from a diamine compound of formula $R^3HN$-G-$NHR^3$. The diamine can have primary or secondary amino groups. In many embodiments, both of the amino groups of the diamine are primary amino groups (i.e., both $R^3$ groups are hydrogen) and the diamine is of formula $H_2N$-G-$NH_2$.

In Formula I, $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group, for example, a 5- to 7-membered ring. In some embodiments, $R^3HN$-G-$NHR^3$ is piperazine. In some embodiments, $R^3$ is hydrogen or an alkyl.

Silicone polyoxamides useful for practicing the present disclosure are typically prepared by reacting a silicone diamine with diethyl oxalate at an elevated temperature. The resulting ethyl oxalate-capped silicone can then be treated with a diamine such as an alkylene diamine, another silicone diamine, an arylene diamine, an alkylarylene diamine, an arylalkylene diamine, or a polyoxyalkylene diamine (e.g., such as those available, for example, from Huntsman, The Woodlands, Tex., under the trade designation "JEFFAMINE". Suitable reaction conditions for preparing a silicone polyoxamide useful for practicing the present disclosure can be found, for example, in U.S. Pat. No. 7,371,464 (Sherman et al.) and U.S. Pat. No. 7,915,370 (Sherman et al.) and the references cited therein. Suitable starting materials for the silicone polyoxamides (e.g., silicone diamines) can be found in these patents and the references cited therein.

In some embodiments, the polydiorganosiloxane polyamide tends to be free of groups having a formula —$R^a$—(CO)—NH— where $R^a$ is an alkylene. Typically, the carbonylamino groups along the backbone of the copolymeric material are part of an oxalylamino group (i.e., the —(CO)—(CO)—NH— group). That is, typically, any carbonyl group along the backbone of the copolymeric material is bonded to another carbonyl group and is part of an oxalyl group.

The silicone polyoxamide may have a variety of number average molecular weights. For example, a silicone polyoxamide having a weight average molecular weight of at least 2000 grams per mole (in some embodiments, at least 3000, 4000, or 5000 grams per mole) may be useful. In some embodiments, the silicone polyoxamide has a weight average molecular weight of up to 60,000 grams per mole (in some embodiments, up to 50,000, 40,000, or 35,000 grams per mole). Useful weight average molecular weights for the silicone polyoxamide may be, for example, in a range from 2,000 grams per mole to 60,000 grams per mole, 3,000 grams per mole to 50,000 grams per mole, or 2,000 grams per mole to 40,000 grams per mole.

In some embodiments, the primer layer cannot be considered a pressure sensitive adhesive as defined above. In some embodiments, the primer layer is substantially free of tackifier, including any of the tackifiers described below. "Substantially free of tackifier" can mean that the primer layer includes a tackifier but in an amount that is insufficient to make the primer layer tacky at room temperature. In some embodiments, "substantially free of tackifier" refers to having up to 10, 5, 2, or 1 percent tackifier by weight, based on the total weight of the primer layer. "Substantially free of tackifier" includes being free of tackifier (that is, having no tackifier present).

The primer layer may be applied to the substrate in a variety of ways. For example, the primer polymer may be may be solution cast by dissolving the polymer in a suitable solvent (e.g., tetrahydrofuran, toluene, hydrocarbons, ethyl acetate, or isopropanol), coating the resulting solution onto the substrate 22, and drying to remove solvent. It is also possible that the primer may be cast into a film using a solventless process (e.g., melt casting). The primer layer 24 (in some embodiments, after drying) may have a thickness of 0.01 micrometer to 4 micrometers (in some embodiments, 50 nanometers to 100 nanometers). For paper substrates, primer layer thickness in a range from 0.5 micrometer to 4 micrometers or 1 micrometer to 3 micrometers may be useful. In some embodiments, the primer layer may be a discontinuous layer on the substrate, which may be deposited on the substrate, for example, by pattern coating. For an effective barrier to the adhesive soaking through the substrate when the substrate is porous (e.g., a nonwoven), the primer layer may be coated at least at 10 g/m², 25 g/m², 30 g/m², or 40 g/m² up to 80 g/m².

Silicone adhesives 16, 26 useful for practicing the present disclosure may be silicone gel adhesives or silicone pressure sensitive adhesives. Some silicone pressure sensitive adhesive compositions useful for practicing the present disclosure are commercially available, for example, from Dow Corning, Midland, Mich., under the trade designation "7735" and from Momentive Performance Materials, Columbus, Ohio, under the trade designation "SILGRIP 6574". Suitable silicone adhesives for medical applications include lightly crosslinked silicone gel adhesives that are soft, tacky, elastic materials with moderate adhesive strength. Silicone gel adhesives typically have excellent wetting characteristics due to their inherent low glass transition temperature, low surface energy, and relatively low storage modulus. The inertness and lack of reactivity of the silicone materials make silicone gels suitable for gentle-to-skin adhesive applications. Additionally, the elastic nature of the crosslinked gel and lack of interaction with hair surfaces debond the adhesives from skin by stretch releasing and further reduces the instances of pain during removal. Some silicone adhesives (e.g., silicone gel adhesives) useful for practicing the present disclosure are commercially available, for example, from Dow Corning under the trade designation "MG 7-9850"; from Wacker Chemie AG, Munich, Germany, under the trade designation "SILPURAN 2130"; from Bluestar Silicones, East Brunswick, N.J., under the trade designations "RT GEL 4317 and "SILBIONE RT GEL 4320"; and from NuSIL Silicone Technology, Carpinteria, Calif., under the trade designations "MED-6345" and "MED-6350".

In some embodiments, the silicone adhesive is not a silicone polyoxamide adhesive. In some embodiments, silicone adhesives useful for practicing the present disclosure are formed by an addition cure reaction between vinyl-terminated poly(dimethylsiloxane) (PDMS) and hydrogen terminated PDMS, in the presence of a hydrosilation catalyst (e.g., platinum complex). Vinyl-terminated and hydrogen terminated PDMS chains are referred to as 'functionalized' silicones due to their specific chemical moieties. Individually, such functional silicones are generally not reactive; however, together they form a reactive silicone system. Additionally, silicate resin tackifiers, such as those described in further detail below, and PDMS with multiple hydrogen functionalities (crosslinkers) can be formulated to modify the adhesive properties of the silicone adhesives. Silicone adhesives resulting from this addition reaction are typically called silicone gel adhesives if they are very lightly crosslinked polydimethysiloxane (PDMS) networks with some level of free (not crosslinked) PDMS fluid and no or low levels of tackifiying resin. By contrast, silicone pressure sensitive adhesives are typically formulated with higher levels of tackifying resins (e.g., 45-60 weight percent). The amount of tackifying resin and control of crosslink density (the chain length of the polymer between the crosslinks) are features that are carefully controlled in silicone adhesives useful for medical articles that will adhere to skin. Silicone adhesives (e.g., silicone gel adhesives) useful for practicing the present disclosure may also include hydroxyl functional groups. Examples of such adhesives are disclosed in Int. Pat. App. Pub. No. WO 2005/102403 (Gantner et al.).

In some embodiments, the silicone adhesive is a radiation crosslinked silicone adhesive, such as those disclosed in U.S. Pat. App. Pub. No. 2011/0212325 (Determan et al.), the disclosure of which is herein incorporated by reference. Radiation crosslinking processes typically require less space and less capital equipment than catalyzed thermal curing processes. Also, radiation crosslinking is typically a faster process than thermal curing, which results in higher throughput and lower manufacturing costs. Radiation curing is typically accomplished through high energy radiation, such as electron beam or gamma ray radiation, as described in U.S. Pat. App. Pub. No. 2011/0212325 (Determan et al.). Reactive functional groups are not required in the adhesive compositions in order to make radiation crosslinked silicone adhesives.

Silicone adhesive compositions, which may be crosslinked to from silicone adhesives in some embodiments of the adhesives articles disclosed herein and the methods of making them, can include silicone oils, fluids, gums, elastomers, or resins. Generally, lower molecular weight, lower viscosity silicone materials are referred to as fluids or oils, while higher molecular weight, higher viscosity materials are referred to as gums; however, there is no sharp distinction between these terms. Silicone elastomers typically have crosslinking (e.g., polar blocks that associate via hydrogen bonding or phase separation) that provides the elasticity. As used herein, the terms "fluid" and "oil" refer to materials having a dynamic viscosity at 25° C. of no greater than 1,000,000 mPa·sec (e.g., less than 600,000 mPa·sec), while materials having a dynamic viscosity at 25° C. of greater than 1,000,000 mPa·sec (e.g., at least 10,000,000 mPa·sec) are referred to as "gums".

Useful adhesive compositions useful for making silicone adhesives in the articles and methods disclosed herein include poly diorganosiloxanes, i.e., materials comprising a polysiloxane backbone. In some embodiments, useful diorganosiloxanes can be described by the following formula illustrating a siloxane backbone with aliphatic and/or aromatic substituents:

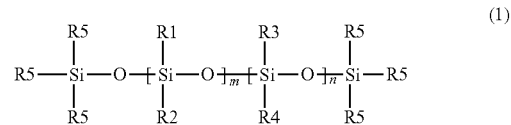

(1)

wherein R1, R2, R3, and R4 are independently selected from the group consisting of an alkyl group and an aryl group, each R5 is an alkyl group and n and m are integers, and at least one of m or n is not zero. In some embodiments, one or more of the alkyl or aryl groups may contain a halogen substituent, e.g., fluorine. For example, in some embodiments, one or more of the alkyl groups may be —$CH_2CH_2C_4F_9$.

In some embodiments, R5 is a methyl group, i.e., the poly diorganosiloxane material is terminated by trimethylsiloxy groups. In some embodiments, R1 and R2 are alkyl groups and n is zero, i.e., the material is a poly(dialkylsiloxane). In some embodiments, the alkyl group is a methyl group, i.e., poly(dimethylsiloxane) ("PDMS"). In some embodiments, R1 is an alkyl group, R2 is an aryl group, and n is zero, i.e., the material is a poly(alkylarylsiloxane). In some embodiments, R1 is methyl group and R2 is a phenyl group, i.e., the material is poly(methylphenylsiloxane). In some embodiments, R1 and R2 are alkyl groups and R3 and R4 are aryl groups, i.e., the material is a poly(dialkyldiarylsiloxane). In some embodiments, R1 and R2 are methyl groups, and R3 and R4 are phenyl groups, i.e., the material is poly(dimethyldiphenylsiloxane).

In some embodiments, the poly diorganosiloxanes may be branched. For example, one or more of the R1, R2, R3, and/or R4 groups may be a linear or branched siloxane with alkyl or aryl (including halogenated alkyl or aryl) substituents and terminal R5 groups.

The poly diorganosiloxanes described above are considered "nonfunctional" since the R1, R2, R3, R4, and R5 groups are nonfunctional groups (e.g., alkyl or aryl groups consisting of carbon, hydrogen, and in some embodiments, halogen (e.g., fluorine) atoms).

In some embodiments, the polysiloxane useful for making silicone adhesives in the articles and methods disclosed herein may be a functional polysiloxane. Functional polysiloxanes include specific reactive groups attached to the polysiloxane backbone of the starting material (e.g., hydrogen, hydroxyl, vinyl, allyl, or acrylic groups). As used herein, a "functionalized poly diorganosiloxane material" is one in which at least one of the R-groups of Formula 2 is a functional group.

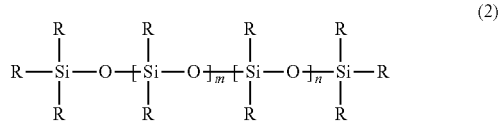
(2)

In some embodiments, a functional poly diorganosiloxane material is one in which at least 2 of the R-groups are functional groups. Generally, the R-groups of Formula 2 may be independently selected. In some embodiments, at least one functional group is selected from the group consisting of a hydride group, a hydroxy group, an alkoxy group, a vinyl group, an epoxy group, and an acrylate group. Typically, a functional polydiorgano siloxane will have a mixture of reactive groups and nonfunctional groups on the polysiloxane backbone. That is, in Formula 2, some of the R groups are reactive groups and others are nonfunctional groups. In some embodiments, the functionalized poly diorganosiloxane materials may be branched. For example, one or more of the R groups may be a linear or branched siloxane with functional and/or non-functional substituents.

In some embodiments, silicone adhesives useful in the articles and methods of the present disclosure may be prepared by combining one or more poly diorganosiloxane materials (e.g., silicone oils or fluids), optionally with an appropriate tackifying resin, coating the resulting adhesive composition on the substrate or primer, and crosslinking the adhesive composition to form the silicone adhesive. In some embodiments, coating the silicone adhesive composition includes pattern coating. Generally, any known additives useful in the formulation of adhesives may also be included.

If included, generally, any known tackifying resin may be used, e.g., in some embodiments, silicate tackifying resins may be used. In some exemplary adhesive compositions, a plurality of silicate tackifying resins can be used to achieve desired performance.

Suitable silicate tackifying resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000-gm/mole, e.g., 500 to 15,000 gm/mole and generally R' groups are methyl groups.

MQ silicate tackifying resins are copolymeric resins where each M unit is bonded to a Q unit, and each Q unit is bonded to at least one other Q unit. Some of the Q units are bonded to only other Q units. However, some Q units are bonded to hydroxyl radicals resulting in $HOSiO_{3/2}$ units (i.e., "$T^{OH}$" units), thereby accounting for some silicon-bonded hydroxyl content of the silicate tackifying resin.

Such resins are described in, for example, *Encyclopedia of Polymer Science and Engineering*, vol. 15, John Wiley & Sons, New York, (1989), pp. 265-270, and U.S. Pat. No. 2,676,182 (Daudt et al.), U.S. Pat. No. 3,627,851 (Brady), U.S. Pat. No. 3,772,247 (Flannigan), and U.S. Pat. No. 5,248,739 (Schmidt et al.). Other examples are disclosed in U.S. Pat. No. 5,082,706 (Tangney). The above-described resins are generally prepared in solvent. Dried or solventless, M silicone tackifying resins can be prepared, as described in U.S. Pat. No. 5,319,040 (Wengrovius et al.), U.S. Pat. No. 5,302,685 (Tsumura et al.), and U.S. Pat. No. 4,935,484 (Wolfgruber et al.). Certain MQ silicate tackifying resins can be prepared by the silica hydrosol capping process described in U.S. Pat. No. 2,676,182 (Daudt et al.) as modified according to U.S. Pat. No. 3,627,851 (Brady), and U.S. Pat. No. 3,772,247 (Flannigan).

The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

MQD silicone tackifying resins are terpolymers having M, Q and D units. In some embodiments, some of the methyl R' groups of the D units can be replaced with vinyl ($CH2=CH—$) groups ("$D^{Vi}$" units). MQD silicone tackifying resins are terpolymers having R3SiO1/2 units ("M" units), SiO4/2 units ("Q" units), and R2SiO2/2 units ("D" units) such as are taught in U.S. Pat. No. 2,736,721 (Dexter). MQT silicate tackifying resins are terpolymers having M, Q and T units. MQT silicate tackifying resins are terpolymers having R3SiO1/2 units, SiO4/2 units and RSiO3/2 units ("T" units) such as are taught in U.S. Pat. No. 5,110,890 (Butler) and Japanese Kokai HE 2-36234.

Suitable silicate tackifying resins are commercially available from sources such as Dow Corning (e.g., under the trade designation "DC 2-7066"), Momentive Performance Materials, Columbus, Ohio, (e.g., under the trade designations "SR545" and "SR1000"), and Wacker Chemie AG (e.g., under the trade designation "BELSIL TMS-803").

The polysiloxane material, the tackifying resin, if present, and any optional additives (e.g., fillers, pigments, additives for improving adhesion, pharmaceutical agents, cosmetic agents, natural extracts, silicone waxes, and rheology modifiers) may be combined by any of a wide variety of known means prior to being coated and crosslinked. For example, in some embodiments, the various components may be pre-blended using common equipment such as mixers, blenders, mills, and extruders.

In some embodiments, the materials may be dissolved in a solvent, coated, and dried prior to crosslinking. In some embodiments, solventless compounding and coating processes may be used. In some embodiments, solventless coating may occur at about room temperature. For example, in some embodiments, the materials may have kinematic viscosity of no greater than 100,000 centistokes (cSt), e.g., no greater than 50,000 cSt. However, in some embodiments, hot melt coating processes such as extrusion may be used, e.g., to reduce the viscosity of higher molecular weight materials to values more suitable for coating. The various components may be added together, in various combinations or individually, through one or more separate ports of an extruder, blended (e.g., melt mixed) within the extruder, and extruded to form the hot melt coated composition.

In some embodiments of the method of making an adhesive article according to the present disclosure, crosslinking the silicone adhesive composition includes exposing the adhesive composition to radiation to form a radiation crosslinked silicone adhesive. Likewise, in some embodiments of the adhesive article according to the present disclosure, the silicone adhesive is a radiation crosslinked silicone adhesive. In some embodiments, the silicone adhesive may be crosslinked through exposure to E-beam irradiation. In some embodiments, the silicone adhesive may be crosslinked through exposure to gamma irradiation. In some embodiments, a combination of electron beam curing and gamma ray curing may be used. For example, in some embodiments, the silicone adhesive may be partially crosslinked by exposure to electron beam irradiation. Subsequently, the silicone adhesive may be further crosslinked by gamma irradiation.

A variety of procedures for E-beam and gamma ray curing may be useful. The crosslinking depends on the specific equipment used, and those skilled in the art can define a dose calibration model for the specific equipment, geometry, and line speed, as well as other process parameters.

Commercially available electron beam generating equipment is readily available. Generally, a support film (e.g., polyester terephthalate support film) runs through a chamber, and the substrates, in some embodiments, with the primers, with the adhesive compositions coated thereon are attached to the support film. Generally, the chamber is inerted (e.g., the oxygen-containing room air is replaced with an inert gas, e.g., nitrogen) while the samples are e-beam crosslinked, particularly when open-face curing (e.g., in the absence of a release liner on top of the adhesive). Single or multiple passes through the chamber may be useful.

Commercially available gamma irradiation equipment includes equipment often used for gamma irradiation sterilization of products for medical applications. In some embodiments, such equipment may be used to crosslink, or partially crosslink the adhesive compositions disclosed herein. In some embodiments, such curing may occur simultaneously with a sterilization process for a semi-finished or finished product, for example a tape or wound dressing.

The thickness of the silicone adhesive in the adhesive articles according to the present disclosure is not particularly limited. In some embodiments, the thickness will be at least 10 microns, and in some embodiments, at least 20 microns. In some embodiments, the thickness will be no greater than 400 microns, and in some embodiments, no greater than 200 microns.

In some embodiments, the adhesive article is suitable for application to skin. Therefore, the adhesive article 10 or 20 can be a medical tape, bandage, or wound dressing. In some embodiments, the adhesive article can be an IV site dressings, a buccal patch, or a transdermal patch. In some embodiments, the adhesive articles according to the present disclosure may be adhered to the skin of humans and/or animals. The adhesive articles according to the present disclosure may include other materials such as polymeric materials, plastics, natural macromolecular materials (e.g., collagen, wood, cork, and leather), paper, films, foams, woven cloth and non-woven cloth, composites, and combinations of these materials.

As the Examples below demonstrate, a silicone polyoxamide primer layer typically increases the strength of the bond between a silicone adhesive and a substrate. The adhesive strength between the silicone adhesive and the substrate is increased such that it either exceeds the cohesive strength of the silicone adhesive or the adhesive strength between the silicone adhesive and the testing tape (3M™ Polyester Tape 8403).

Some useful primers can contain reactive functional groups (e.g., epoxy, acrylic, isocyanate, vinyl, or hydrolysable silanes) to form covalent bonds with a substrate and/or an adhesive coated onto the substrate. Still other methods for improving adhesion between a substrate and an adhesive include plasma treatment, corona treatment, or flame treatment of a substrate surface to clean or roughen the surface and/or provide polar functional groups on the surface. In contrast, in the adhesive articles according to and/or made according to the present disclosure, the adhesive strength between the substrate and the adhesive is improved even though the silicone polyoxamide do not contain reactive functional groups to promote interaction with the substrate or the adhesive. An extra step of plasma, corona, or flame treatment of the substrate surface is not required for the adhesive articles disclosed herein.

Furthermore, as shown in the examples below, silicone polyoxamide in some cases is a better primer (that is, provides better adhesion between a silicone adhesive and a substrate) than conventional primers used for silicone adhesives.

Some Embodiments of the Disclosure

In a first embodiment, the present disclosure provides an adhesive article comprising:

a substrate;

a primer layer disposed on the substrate, wherein the primer layer comprises a silicone polyoxamide; and a silicone adhesive disposed on the primer layer.

In a second embodiment, the present disclosure provides the adhesive article of the first embodiment, wherein the primer layer is essentially free of tackifier.

In a third embodiment, the present disclosure provides the adhesive article of the first or second embodiment, wherein the substrate comprises a thermoplastic, wherein the substrate is a paper substrate, or wherein the substrate is a nonwoven.

In a fourth embodiment, the present disclosure provides the adhesive article of the third embodiment, wherein the thermoplastic is a polyolefin, a polyester, a polyurethane, or an ethylene-vinyl acetate copolymer.

In a fifth embodiment, the present disclosure provides the adhesive article of any one of the first to fourth embodiments, wherein the silicone polyoxamide has at least two repeat units represented by Formula I:

$$\left[\begin{array}{c}\phantom{x}\\ *-N-Y-\underset{\underset{R^1}{|}}{\overset{\overset{R^1}{|}}{Si}}-\left[O-\underset{\underset{R^1}{|}}{\overset{\overset{R^1}{|}}{Si}}\right]_n-O-\underset{\underset{R^1}{|}}{\overset{\overset{R^1}{|}}{Si}}-Y-\underset{H}{N}-\overset{\overset{O}{||}}{C}-\overset{\overset{O}{||}}{C}\\ \phantom{x}\end{array}\right]_p-\underset{\underset{R^3}{|}}{N}-G-\underset{\underset{R^3}{|}}{N}-\overset{\overset{O}{||}}{C}-\overset{\overset{O}{||}}{C}-*\qquad\text{I}$$

wherein each $R^1$ is independently an alkyl, haloalkyl, arylalkylenyl, alkenyl, aryl, or aryl substituted with an alkyl, alkoxy, or halo;

each Y is independently an alkylene, alkylarylene, or arylalkylene;

each G is independently alkylene, arylene, arylalkylene, alkylarylene, polyoxyalkyene, or polydiorganosiloxane;

$R^3$ is hydrogen or alkyl or $R^3$ taken together with G and with the nitrogen to which they are both attached forms a heterocyclic group;

n is independently an integer of 40 to 1500;

p is an integer of 1 to 10; and an asterisk (*) indicates a site of attachment of the repeat unit to another group in the copolymer.

In a sixth embodiment, the present disclosure provides the adhesive article of the fifth embodiment, wherein at least 50 percent of the R' groups are methyl, each Y is independently alkylene, each G is independently alkylene, arylene, or polyoxyalkylene, and each $R^3$ is hydrogen.

In a seventh embodiment, the present disclosure provides the adhesive article of the fifth or sixth embodiment, wherein the silicone polyoxamide has a number average molecular weight in a range from 2000 grams per mole to 40,000 grams per mole.

In an eighth embodiment, the present disclosure provides the adhesive article of any one of the first to seventh embodiments, wherein the silicone adhesive is a radiation-crosslinked silicone adhesive.

In a ninth embodiment, the present disclosure provides the adhesive article of any one of the first to eighth embodiments, wherein the silicone adhesive comprises a crosslinked poly(diorganosiloxane).

In a tenth embodiment, the present disclosure provides the adhesive article of any one of the first to ninth embodiments, wherein the silicone adhesive is a crosslinked poly(diorganosiloxane) comprising silanol, alkyl, or aryl terminal groups or a combination thereof, and wherein alkyl and aryl are optionally halogenated.

In an eleventh embodiment, the present disclosure provides the adhesive article of any one of the first to tenth embodiments, wherein the silicone adhesive comprises a silicate resin tackifier.

In a twelfth embodiment, the present disclosure provides the adhesive article of any one of the first to eleventh embodiments, wherein the silicone adhesive is not a silicone polyoxamide adhesive.

In a thirteenth embodiment, the present disclosure provides the adhesive article of any of the first to twelfth embodiments, wherein the adhesive article is a bandage, tape, or wound dressing.

In a fourteenth embodiment, the present disclosure provides method of making the adhesive article of any one of the first to thirteenth embodiments, the method comprising:

coating the primer layer onto the substrate;

coating a silicone adhesive composition onto the primer layer; and crosslinking the silicone adhesive composition to form the silicone adhesive.

In a fifteenth embodiment, the present disclosure provides the method of the fourteenth embodiment, wherein coating the primer layer comprises pattern-coating.

In a sixteenth embodiment, the present disclosure provides the method of the fourteenth or fifteenth embodiment, wherein coating the silicone adhesive composition comprises pattern-coating.

In a seventeenth embodiment, the present disclosure provides the method of any of the fourteenth to sixteenth embodiments, wherein the primer layer improves adhesion between the substrate and the silicone adhesive.

In an eighteenth embodiment, the present disclosure provides the method of any of the fourteenth to seventeenth embodiments, wherein crosslinking the silicone adhesive composition comprises exposing the silicone adhesive composition to radiation to form a radiation-crosslinked silicone adhesive.

In a nineteenth embodiment, the present disclosure provides the method of the eighteenth embodiment, wherein the radiation comprises at least one of electron-beam or gamma radiation.

In a twentieth embodiment, the present disclosure provides the use of a silicone polyoxamide as a primer for improving adhesion between a substrate and a silicone adhesive. The twentieth embodiment may also be understood as a primer composition for improving adhesion between a substrate and a silicone adhesive, wherein the primer composition comprises a silicone polyoxamide.

In a twenty-first embodiment, the present disclosure provides the use of the twentieth embodiment, wherein the silicone polyoxamide is essentially free of tackifier.

In a twenty-second embodiment, the present disclosure provides the use of the twentieth or twenty-first embodiment, wherein the substrate comprises a thermoplastic, wherein the substrate is a paper substrate, or wherein the substrate is a nonwoven.

In a twenty-third embodiment, the present disclosure provides the use of the twenty-second embodiment, wherein the thermoplastic is a polyolefin, a polyester, a polyurethane, or an ethylene-vinyl acetate copolymer.

In a twenty-fourth embodiment, the present disclosure provides the use of any one of the twentieth to twenty-third embodiments, wherein the silicone polyoxamide has at least two repeat units represented by Formula I:

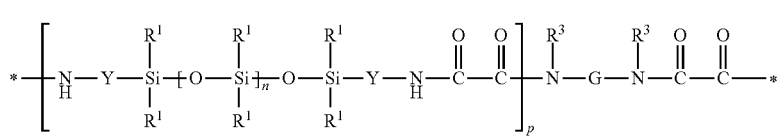

wherein
each $R^1$ is independently an alkyl, haloalkyl, arylalkylenyl, alkenyl, aryl, or aryl substituted with an alkyl, alkoxy, or halo;
each Y is independently an alkylene, alkylarylene, or arylalkylene;
each G is independently alkylene, arylene, arylalkylene, alkylarylene, polyoxyalkyene, or polydiorganosiloxane;
$R^3$ is hydrogen or alkyl or $R^3$ taken together with G and with the nitrogen to which they are both attached forms a heterocyclic group;
n is independently an integer of 40 to 1500;
p is an integer of 1 to 10; and
an asterisk (*) indicates a site of attachment of the repeat unit to another group in the copolymer.

In a twenty-fifth embodiment, the present disclosure provides the use of the twenty-fourth embodiment, wherein at least 50 percent of the $R^1$ groups are methyl, each Y is independently alkylene, each G is independently alkylene or polyoxyalkylene, and each $R^3$ is hydrogen.

In a twenty-sixth embodiment, the present disclosure provides the use of the twenty-fourth or twenty-fifth embodiment, wherein the silicone polyoxamide has a number average molecular weight in a range from 2000 grams per mole to 40,000 grams per mole.

In a twenty-seventh embodiment, the present disclosure provides the use of any one of the twentieth to twenty-sixth embodiments, wherein the silicone adhesive is a radiation-crosslinked silicone adhesive.

In a twenty-eighth embodiment, the present disclosure provides the use of any one of the twentieth to twenty-seventh embodiments, wherein the silicone adhesive comprises a crosslinked poly(diorganosiloxane).

In a twenty-ninth embodiment, the present disclosure provides the use of any one of the twentieth to twenty-eighth embodiments, wherein the silicone adhesive is a crosslinked poly(diorganosiloxane) comprising silanol, alkyl, or aryl terminal groups or a combination thereof, and wherein alkyl and aryl are optionally halogenated.

In a thirtieth embodiment, the present disclosure provides the use of any one of the twentieth to twenty-ninth embodiments, wherein the silicone adhesive comprises a silicate resin tackifier.

In a thirty-first embodiment, the present disclosure provides the use of any one of the twentieth to thirtieth embodiments, wherein the silicone adhesive is not a silicone polyoxamide adhesive.

EXAMPLES

The present disclosure is further illustrated by the following examples, but the particular materials and amounts thereof recited in these examples, as well as other conditions and details, should not be construed to unduly limit this invention.

Materials

Materials utilized in the following examples are shown in Table 1.

TABLE 1

| Component | Source | Description |
| --- | --- | --- |
| SPOx | 3M Company, St. Paul, MN | Silicone polyoxamide, prepared per U.S. Pat. No. 7,915,370, Preparative Example 1 |
| "XIAMETER ™ OHX-4070" | Dow Corning, Midland, MI | "XIAMETER ™ OHX-4070", silicone fluid, 50,000 cSt viscosity |
| "MQ803TF" | Wacker Chemical Corp., Adrian, MI | Co-hydrolysis product of tetraalkoxy silane (Q unit) and trimethyl-ethoxy silane (M unit) |
| Paper | 3M Company, St. Paul, MN | 34 lb/ream crepe paper saturated with an SBR-based latex, seal coated with a latex acrylate, coated with an acrylate-based LAB |
| PET | Mitsubishi, Greer, SC | "HOSTAPHAN ™ 3SAB" polyester film |
| PE/PP | Blako Industries, Dunbridge, OH | "COTHENE ™" polypropylene/polyethylene film, 3.1 mil thick |
| LDPE | 3M Company, St. Paul, MN | Low density polyethylene backing |
| EVA | 3M Company, St. Paul, MN | Ethylene-vinyl acetate, 4 mil thick |
| EXACT 0230 | Exxon Mobil Chemical | Ethylene-based plastomer resin |
| "PRIMER 94" | 3M Company, St. Paul, MN | 3M ™ "TAPE PRIMER 94" |

Test Methods

Peel Force

The bond strength between the adhesive and backing was determined by laminating a 2-4 inch section of 3M™ Polyester Tape 8403 to the adhesive side of the sample tapes. The "8403" tape was applied with 2 passes of a 2 kg roller at 30.5 cm/min and allowed to dwell for 5-30 minutes. The "8403" tape was removed at 30.5 cm/min at 180 degrees with an IMASS SP2000 Slip/Peel Tester (IMASS, Inc., Accord, Mass.). The peel force was recorded.

Appearance

The appearance is a visual assessment of the adhesive/backing bond strength. After the Peel Force test was completed, the backing was inspected for adhesive residue. A "fail" indicates the adhesive was cleanly removed from the backing, with no adhesive residue left on the backing. A "pass" indicates the adhesive cohesively split, leaving residue on the backing and on the "8403" tape. Pass indicates the bond strength between the adhesive and the backing is greater than the cohesive strength of the adhesive.

Example 1 (E-1)

Primer

A 5% solids solution of the SPOx in 70/30 toluene/isopropanol was applied to a PET backing with a #6 Mayer rod. The coated PET was then dried at 70° C. for 10 minutes.

Adhesive

A blend of "OHX-4070" and "MQ803TF" in the weight ratio of 62/38 was prepared. The blend was coated on the backing using conventional coating methods and further crosslinked with e-beam irradiation to form a tacky film. The radiation processing was performed on a Model 40767 electron beam generating apparatus (PCT, Davenport, Iowa). A support film (polyethylene terephthalate) was run through the inerted chamber of the apparatus. The adhesives coated on the primed backings were attached to the support film and conveyed at a fixed speed of about 9 meters/min through the e-beam apparatus. The adhesive and process is described in U.S. Pat. App. Pub. No. 2011/0212325 (Determan et al.).

Examples 2 Through 8 (E-2 Through E-8)

Examples 2 to 8 were prepared as in Example 1, with the following exceptions. A #14 Mayer rod was used for coating the primer on the backing. The ratio of "OHX-4070" to "MQ803TF" in the adhesive was 69/31 for the PE/PP backing and 82/18 for the LDPE and EVA backing.

Comparative Examples 1 Through 5 (C-1 Through C-5)

Comparative Examples 1 to 5 were prepared as in Example 1 with the exception that no primer was utilized. The ratio of "OHX-4070" to "MQ 803TF" in the adhesive was 69/31 for the PE/PP backing and 82/18 for the LDPE and EVA backing.

Comparative Example 6 (C-6)

Comparative Example 6 was prepared as in Example 1, with the following exception: "PRIMER 94" was used instead of SPOx as the primer.

The weight average molecular weight of the SPOx primer that was used, the backing, the peel force, and appearance of the adhesive for each Example and Comparative Example are shown in Table 2. In the table, "k" refers to thousands. That is, 5K is 5000 and so forth.

TABLE 2

| Sample | Backing | Primer | Appearance | Peel Force (g/cm) |
| --- | --- | --- | --- | --- |
| E-1 | PET | 5k SPOx | Pass | 239 |
| E-2 | PE/PP | 5k SPOx | Pass | 155 |
| E-3 | LDPE | 5k SPOx | Pass | 170 |
| E-4 | Paper | 5k SPOx | Pass | 226 |
| E-5 | Paper | 14k SPOx | Pass | 201 |
| E-6 | Paper | 25k SPOx | Pass | 178 |
| E-7 | Paper | 33k SPOx | Pass | 152 |
| E-8 | EVA | 5k SPOx | Pass | 109 |
| C-1 | PET | None | Fail | 69 |
| C-2 | PE/PP | None | Fail | 37 |
| C-3 | LDPE | None | Fail | 61 |
| C-4 | Paper | None | Fail | 95 |
| C-5 | EVA | None | Fail | 84 |
| C-6 | Paper | "PRIMER 94" | Fail | [a] |

[a] Not measured

Example 9

Example 9 was prepared as in Example 1, with the following exceptions. An 18% solids solution of 5 k SPOx in 70/30 toluene/isopropanol was applied using a notch bar coater to a porous LLPE nonwoven backing having a basis weight of 80 g/m$^2$. The coated nonwoven was then dried at 70° C. for 10 minutes. This SPOx barrier coating was measured to be 40 g/m$^2$. The ratio of "OHX-4070" to "MQ803TF" in the adhesive was 69/31. The adhesive coat weight was measured to be 150 g/m$^2$. The sample was tested and passed the visual assessment. The peel force was measured to be 142 g/cm. Furthermore, the SPOx coating was found to be an effective barrier to prevent the adhesive from soaking through to the other side of the nonwoven backing.

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein.

What is claimed is:

1. An adhesive article comprising:

a substrate;

a primer layer disposed on the substrate, wherein the primer layer comprises a silicone polyoxamide; and a silicone adhesive disposed on the primer layer.

2. The adhesive article of claim 1, wherein the primer layer is essentially free of tackifier.

3. The adhesive article of claim 1, wherein the substrate comprises a thermoplastic, wherein the substrate is a paper substrate, or wherein the substrate is a nonwoven.

4. The adhesive article of claim 3, wherein the thermoplastic is a polyolefin, a polyester, a polyurethane, or an ethylene-vinyl acetate copolymer.

5. The adhesive article of claim 1, wherein the silicone polyoxamide has at least two repeat units represented by Formula I:

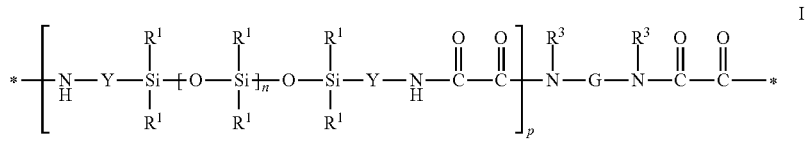

wherein
- each $R^1$ is independently an alkyl, haloalkyl, arylalkylenyl, alkenyl, aryl, or aryl substituted with an alkyl, alkoxy, or halo;
- each Y is independently an alkylene, alkylarylene, or arylalkylene;
- each G is independently alkylene, arylene, arylalkylene, alkylarylene, polyoxyalkyene, or polydiorganosiloxane;
- $R^3$ is hydrogen or alkyl or $R^3$ taken together with G and with the nitrogen to which they are both attached forms a heterocyclic group;
- n is independently an integer of 40 to 1500;
- p is an integer of 1 to 10; and
- an asterisk (*) indicates a site of attachment of the repeat unit to another group in the copolymer.

6. The adhesive article of claim 5, wherein at least 50 percent of the $R^1$ groups are methyl, each Y is independently alkylene, each G is independently alkylene, arylene, or polyoxyalkylene, and each $R^3$ is hydrogen.

7. The adhesive article of claim 1, wherein the silicone adhesive is a radiation-crosslinked silicone adhesive.

8. The adhesive article of claim 1, wherein the silicone adhesive is a crosslinked poly(diorganosiloxane) comprising silanol, alkyl, or aryl terminal groups or a combination thereof, and wherein alkyl and aryl are optionally halogenated.

9. The adhesive article of claim 1, wherein the adhesive article is a bandage, medical tape, or wound dressing.

10. A method of making the adhesive article of claim 1, the method comprising:
- coating the primer layer onto the substrate;
- coating a silicone adhesive composition onto the primer layer; and
- crosslinking the silicone adhesive composition to form the silicone adhesive.

11. The method of claim 10, wherein at least one of coating the primer layer or coating the silicone adhesive composition comprises pattern-coating.

12. The method of claim 10, wherein the primer layer improves adhesion between the substrate and the silicone adhesive.

13. The method of claim 10, wherein crosslinking the silicone adhesive composition comprises exposing the silicone adhesive composition to radiation to form the silicone adhesive.

14. A method for improving adhesion between a substrate and a silicone adhesive, the method comprising:
- coating a primer layer comprising a silicone polyoxamide onto the substrate;
- coating a silicone adhesive composition onto the primer layer; and
- crosslinking the silicone adhesive composition to form the silicone adhesive.

15. The method of claim 14, wherein the silicone adhesive is a radiation-crosslinked silicone adhesive.

16. The method of claim 13, wherein the radiation comprises at least one of electron-beam or gamma radiation.

17. The adhesive article of claim 5, wherein the silicone polyoxamide has a number average molecular weight in a range from 2000 grams per mole to 40,000 grams per mole.

18. The adhesive article of claim 1, wherein the silicone adhesive comprises a crosslinked poly(diorganosiloxane).

19. The adhesive article of claim 1, wherein the silicone adhesive comprises a silicate resin tackifier.

20. The adhesive article of claim 1, wherein the silicone adhesive is not a silicone polyoxamide adhesive.

* * * * *